(12) United States Patent
Trainoff et al.

(10) Patent No.: US 9,274,044 B2
(45) Date of Patent: Mar. 1, 2016

(54) CUVETTE FOR LIGHT SCATTERING MEASUREMENTS INCORPORATING EVAPORATION INHIBITION MEANS

(71) Applicants: Steven P. Trainoff, Goleta, CA (US); Michael W. Dewey, Sausalito, CA (US); Aym M. Berges, Santa Barbara, CA (US)

(72) Inventors: Steven P. Trainoff, Goleta, CA (US); Michael W. Dewey, Sausalito, CA (US); Aym M. Berges, Santa Barbara, CA (US)

(73) Assignee: WYATT TECHNOLOGY CORPORATION, Santa Barbara, CA (US)

( * ) Notice: Subject to any disclaimer, the term of this patent is extended or adjusted under 35 U.S.C. 154(b) by 0 days.

(21) Appl. No.: 14/092,288

(22) Filed: Nov. 27, 2013

(65) Prior Publication Data

US 2014/0146313 A1    May 29, 2014

Related U.S. Application Data

(60) Provisional application No. 61/730,921, filed on Nov. 28, 2012.

(51) Int. Cl.
*G01N 21/03* (2006.01)
*G01N 21/51* (2006.01)

(52) U.S. Cl.
CPC ........... *G01N 21/03* (2013.01); *B01L 2200/142* (2013.01); *G01N 21/51* (2013.01); *G01N 2021/0378* (2013.01)

(58) Field of Classification Search
CPC .......... G01N 21/03; G01N 2021/0339; G01N 2021/0378; G01N 2021/0385; B01L 2200/142; C12M 23/08; C12M 23/06

USPC ......................................................... 356/246
See application file for complete search history.

(56) References Cited

U.S. PATENT DOCUMENTS

| | | | | |
|---|---|---|---|---|
| 4,021,124 | A | * | 5/1977 | Sarstedt ..................... 356/246 |
| 4,076,592 | A | * | 2/1978 | Bradley ................ C12M 41/36 422/421 |
| 4,227,810 | A | * | 10/1980 | Sandrock et al. ............. 356/246 |

(Continued)

OTHER PUBLICATIONS

Wyatt Technology Corporation, MicroCUVETTE & NanoFilter Accessory Kits, promotional literature, 2006, Wyatt Technology Corporation, Goleta, USA.

(Continued)

*Primary Examiner* — Michael P LaPage
(74) *Attorney, Agent, or Firm* — David N. Villalpando; Philip J. Wyatt (57) ABSTRACT

A cuvette for use with light scattering detectors is disclosed. A trough or moat within the cuvette can be filled with solvent which is not in fluid contact with the sample to be measured. This solvent moat creates saturated vapor pressure in the chamber preventing evaporation from the sample when the cuvette is capped. The cuvette itself may be made of an inexpensive polymer which can be polished to high optical quality while still being moldable in complex forms capable of enabling further utility, such as extra griping surfaces, identification tabs allowing the detection instrument to determine the cuvette model, and various sample chamber forms. The novel cuvette may have extremely small sample volumes, while allowing significant overfill of the measurement chamber, improving ease of sample loading. The polymers used may be relatively inexpensive, and therefore the cuvette can generally be discarded after a single use.

14 Claims, 5 Drawing Sheets

(56) References Cited

U.S. PATENT DOCUMENTS

| | | | | |
|---|---|---|---|---|
| 4,640,895 A | * | 2/1987 | Davis | C12M 23/08 215/6 |
| 4,735,502 A | * | 4/1988 | Kaufmann | G01N 21/07 356/246 |
| 5,128,104 A | * | 7/1992 | Murphy | B01L 3/502 206/221 |
| 6,249,345 B1 | * | 6/2001 | Kraack et al. | 356/246 |
| 6,458,526 B1 | * | 10/2002 | Schembri et al. | 435/4 |
| 6,660,228 B1 | * | 12/2003 | Chang et al. | 422/68.1 |
| D621,520 S | | 8/2010 | Talmer et al. | |
| 8,110,160 B2 | | 2/2012 | Assmann et al. | |
| 2001/0046702 A1 | * | 11/2001 | Schembri | 435/287.2 |
| 2002/0155617 A1 | * | 10/2002 | Pham et al. | 436/165 |
| 2013/0314697 A1 | * | 11/2013 | Voit et al. | 356/51 |
| 2014/0085628 A1 | * | 3/2014 | McMillan et al. | 356/213 |

OTHER PUBLICATIONS

Hampton Research, Crystallization Mushroom product information, www.hamptonresearch.com, 2012, Hampton Research, Aliso Viejo, USA.

* cited by examiner

PRIOR ART

FIGURE 1 a) Side view            b) Top view

FIGURE 2 a) Front view b) Side view c) Top view

CUVETTE FOR LIGHT SCATTERING MEASUREMENTS INCORPORATING EVAPORATION INHIBITION MEANS

BACKGROUND

Light scattering (LS) is a non-invasive technique for characterizing macromolecules and a wide range of particles in solution. The two types of light scattering detection frequently used for the characterization of macromolecules are static light scattering (SLS) and dynamic light scattering (DLS).

Static light scattering includes a variety of embodiments such as single angle light scattering (SALS), dual angle light scattering (DALS), low angle light scattering (LALS), and multi-angle light scattering (MALS). SLS experiments generally involve the measurement of the absolute intensity of the light scattered from a sample in solution that is illuminated by a fine beam of light. This measurement is often used, for appropriate classes of particles/molecules, to determine the size and structure of the sample molecules or particles, and, when combined with knowledge of the sample concentration, the determination of weight average molar mass. In addition, nonlinearity of the intensity of scattered light as a function of sample concentration may be used to measure interparticle interactions and associations.

Dynamic light scattering is also known as quasi-elastic light scattering (QELS) and photon correlation spectroscopy (PCS). In a DLS experiment, time-dependent fluctuations in the scattered light signal are measured using a fast photodetector. DLS measurements determine the diffusion coefficient of the molecules or particles, which can in turn be used to calculate their hydrodynamic radius.

Extensive literature has been published describing methods for making both static and dynamic light scattering measurements in flowing and batch (non-flowing) systems. See, for example, P. J. Wyatt, "Light scattering and the absolute characterization of macromolecules," *Analytica chimica Acta*, 272, 1-40, (1993). Historically light scattering measurements in batch mode were performed on sample solutions contained in scintillation vials. However, these measurements generally required at least 4 mL of the sample. The flow mode alternative might require a lower sample volume within the flow cell itself, however, a significant amount of sample is still required to deliver and fill the measurement volume of the cell. More recently, cuvettes have been introduced with significantly smaller sample volumes. For example, the MicroCUVETTE manufactured by Wyatt Technology Corporation (Santa Barbara, Calif.) is capable of batch LS measurements with sample volumes as small as 12 µL. A common source of small cuvettes are the so-called microtiter plates containing an array of wells, each of which may serve as a cuvette.

As sample volumes decrease, the likelihood of solvent evaporation also becomes a concern and, as light scattering measurements can be very sensitive to the concentration of the solute with the sample, preventing evaporation can become a critical component of accurate LS measurements. It is an objective of the present invention to minimize sample evaporation for batch light scattering measurements. Evaporation can alter the sample state, skew results through altered background intensity, or prevent light scattering measurements entirely. Partial evaporation of the solvent from a cuvette produces an effective increase of the dissolved solute concentration which additionally may have deleterious effects on the sample itself. Evaporation can also impact the meniscus curvature as well as meniscus height in the cuvette or plate well. More substantial evaporation of the sample solvent may prevent any type of LS measurement, a problem particularly prevalent in very small volume cuvettes where even a small amount of evaporation results in a large change in the height of the fluid level. This can cause the meniscus to be intersected by the incident light beam, overwhelming the detector or detectors and distorting significantly any measurements. Further, temperature dependent measurements during which the cuvette environment is cycled over a broad range of ambient temperatures may promote evaporation thus skewing the results and giving inaccurate data regarding temperature dependent reactions, such as molecular interaction experiments.

A frequently used method to overcome the evaporation problem is to cap or place a film over the mouth of the cuvette itself or to place a layer of oil overlaying the sample contained in each well in a microtiter plate. However, for light scattering measurements, both of these commonly used evaporation mitigation techniques can be problematic. With respect to the cap, the sample solvent may still evaporate and condense on the inner surface of the film or cover as the unused volume of the cuvette itself will have a lower vapor pressure than the sample itself, thus evaporation cannot be mitigated by sealing the cuvette alone. While the use of an oil overlay eliminates the issue of condensation, the potentially negative interactions of oil and sample molecules are well known, as documented in the 2004 article by L. S. Jones et al, "Silicone oil induced aggregation of proteins," published in the Journal of Pharmaceutical Sciences, volume 94, pages 918-927. Such unintended interactions may result in an inaccurate representation of the true sample characteristics. In addition, oil overlays can be difficult to apply, and difficult to remove if the cuvette or well plate is to be reused. It is another objective of the present invention to obviate the need to use an oil overlay to control evaporation in a sample cuvette.

Traditionally, LS measurement cuvettes have been constructed of expensive materials such as quartz and other highly polished glass materials. These cuvettes are often prohibitively expensive to be disposed of after a single use, and therefore must be carefully cleaned between uses to prevent contamination by a prior sample or cleaning agent with the new sample to be analyzed. Further, cuvettes formed from glass substances are rarely capable of being designed in complex forms which would otherwise be useful in providing important benefits to light scattering measurements. It is an objective of the present invention to provide a cuvette compatible with light scattering measurements that is inexpensive enough that it may be discarded after a single use. It is a further objective of this invention to provide a cuvette capable of improved simplicity of use and utility heretofore unavailable in cuvettes made of glass and similar materials.

The limitations disclosed above can seriously inhibit the accurate collection of light scattering data from samples contained within small cuvettes as well as complicating the measurement process by requiring laborious and often inadequate cleaning of the sample containing chamber within the cuvette. A primary objective of the present invention is to provide a means by which all of these limitations for making light scattering measurements in a cuvette may be mitigated, allowing for an increased quality of optical measurements of liquid samples contained therein, while simultaneously facilitating the measurements themselves.

BRIEF DESCRIPTION OF THE INVENTION

A new cuvette which may be used with light scattering instruments is disclosed. One embodiment of the inventive cuvette makes use of one or more troughs which may also be configured as a "moat" contained within the cuvette distinct from the sample chamber of the cuvette, thus any fluid contained within the moat or trough is not in fluid contact with the sample. This moat, when filled with solvent and when the cuvette is capped creates saturated vapor pressure in the chamber, preventing evaporation from the sample itself. The cuvette itself may be made of a polymer which can be polished to high optical quality, such as Cyclic Olefin Copolymer (COC), while still being moldable in complex forms capable of adding further utility to the cuvette. Such complex forms may include embodiments wherein an extra grip is added near the top of the vessel facilitating the insertion and removal of the cuvette from measurement instrumentation. It also permits the inclusion of identification tabs, or keys, which allow a light scattering instrument to determine that a particular form of the cuvette is present. The novel cuvette may have extremely small sample volumes, while allowing significant overfill, improving ease of sample loading. As the polymers which may be used for various embodiments of the novel cuvette are relatively inexpensive to manufacture, the cuvette may generally be discarded after a single use, obviating the need to undertake the laborious and difficult task of cleaning it after every sample measurement. Further, the ability to minimize evaporation from the sample itself by means of the moat design facilitates temperature dependence measurements as well as association measurements which can be highly dependent on sample concentration.

BRIEF DESCRIPTION OF THE DRAWINGS

FIG. 2(b) also indicates elements which may be used in light scattering measurements.

DETAILED DESCRIPTION OF THE INVENTION

Figure 1:
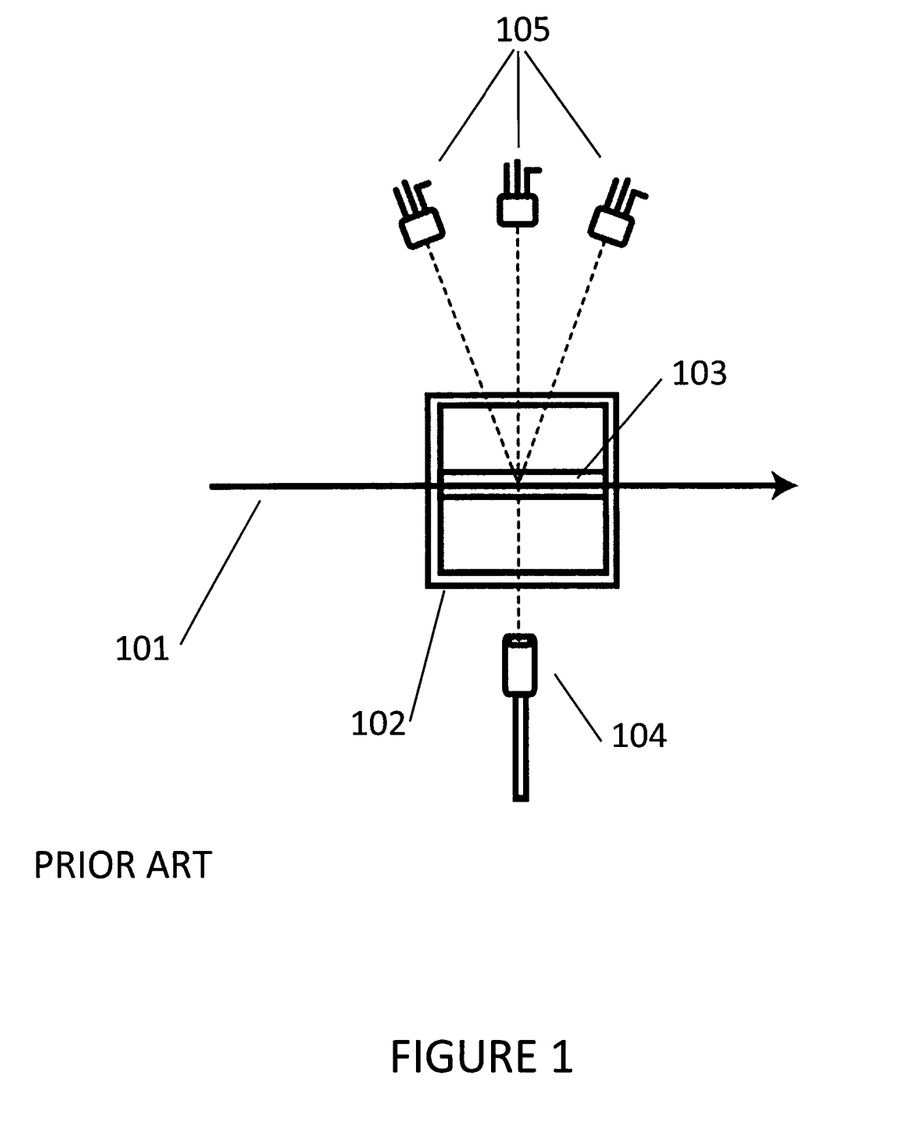
FIG. 1 is a top view of a multiangle light scattering/dynamic light scattering measurement set-up as performed in a conventional cuvette.

Cuvettes can be suitable sample vessels for the measurement of both Dynamic Light Scattering (DLS) and Static Light Scattering (SLS) at a single or multiple angles (MALS). A cutaway top view of a cuvette arranged for such light scattering measurements is shown in FIG. 1. A light beam 101, generally produced by a laser, is directed into the cuvette body 102, through an optically transparent surface, thereby passing through the sample contained within the sample measurement chamber 103. For the case of DLS measurements, a light scattering detector 104, generally an avalanche photo-diode (APD) coupled to a light fiber, is used to collect scattered light. SLS measurements may be made at any number of angles by using one or more appropriate photodetectors 105, such as a photodiode, often a silicon PIN photodiode. These SLS and DLS detectors may exist on the same side or on opposite sides of the cuvette from each other or in other configurations. The detectors are generally arranged in the same plane, and generally view the same scattering volume within the sample measurement chamber 103. The DLS detector 104 is generally oriented at 90° to the light beam 101 but may operate at other angles as well. The cuvette 102 may be made of a material which is insoluble to the sample solvent, such as a synthetic polymer, glass, or fused Spectrosil® quartz.

Figure 2:
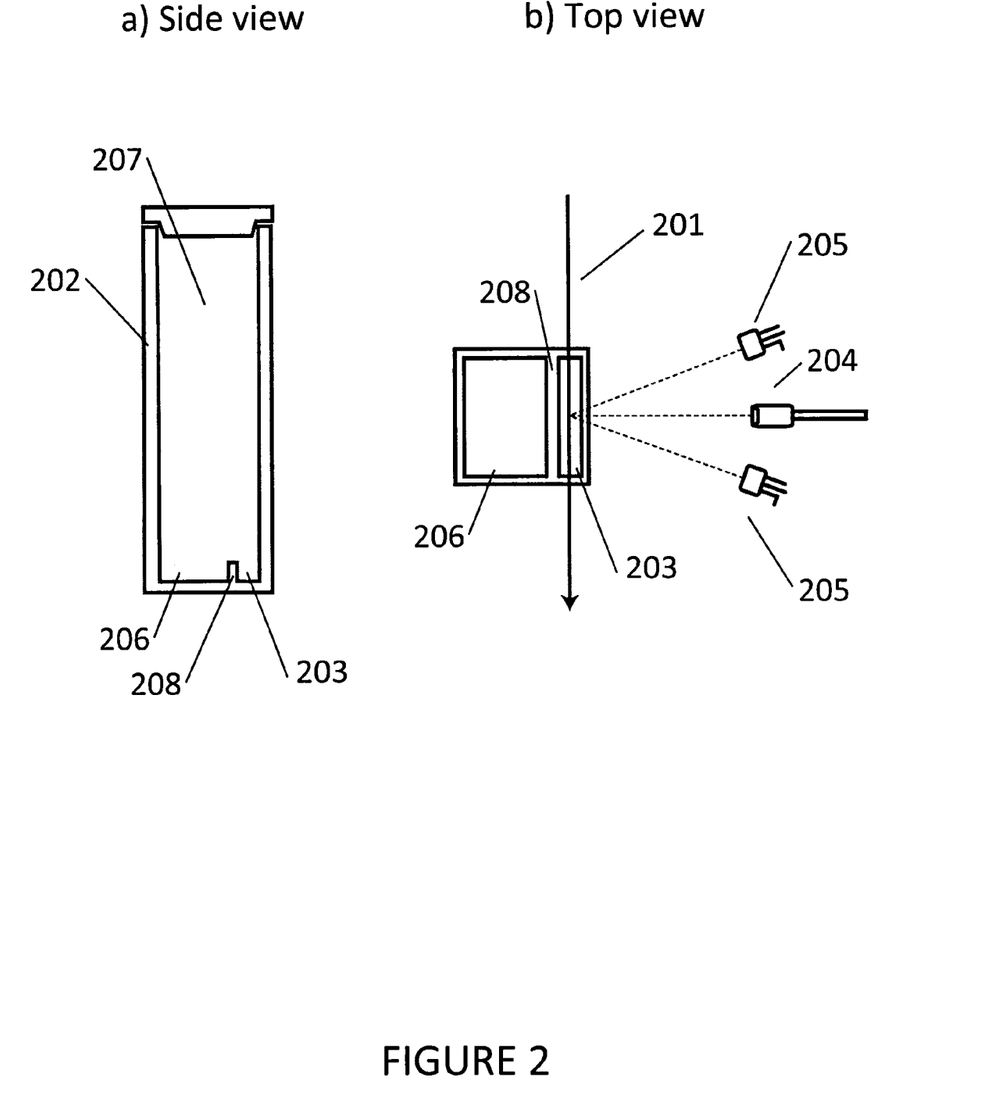
FIG. 2 shows side view (a) and top view (b) cross-sections of an embodiment of the present invention wherein the cuvette has a broad solvent moat and a small sample measurement chamber.

As discussed above, evaporation can have many deleterious effects on the measurement of the light scattering properties of a sample. The novel cuvette of the present invention makes use of a trough which can be filled with a volume of solvent which, when the cuvette is capped, allows the empty volume of the cuvette to reach a stable, saturated vapor pressure which prevents further evaporation from the sample. A simple embodiment of the present invention is shown in FIG. 2. The sample is injected into the sample measurement chamber 203 of the cuvette 202, while a solvent, generally the pure solvent used in the sample solution, is placed within the trough region 206. The light beam 201 passes through the sample measurement chamber 203, and light scattering detectors 204 (DLS) and 205 (SLS) detect light scattered from the sample. A cuvette cap 207 prevents evaporation out of the cuvette into the environment and allows the empty space within the cuvette to reach a saturated vapor pressure. The sample measurement chamber must be at least large enough in cross section for the entire beam diameter of the light beam 201 to pass there through, and, in order to obtain a reliable measurement of the light scattering properties of the sample contained therein, the beam must not intersect the meniscus of the sample, which may occur even if the sample is loaded properly into the sample measurement chamber 203 if the sample partially evaporates. Elements of the cuvette 202, such as the barrier 208 between the sample measurement chamber 203 and the trough 206 may be made of a light absorbing material, such as black glass or a dye infused polymer selected to absorb at the wavelength of the light beam 201, in order to prevent back reflection of scattered light.

Figure 3:
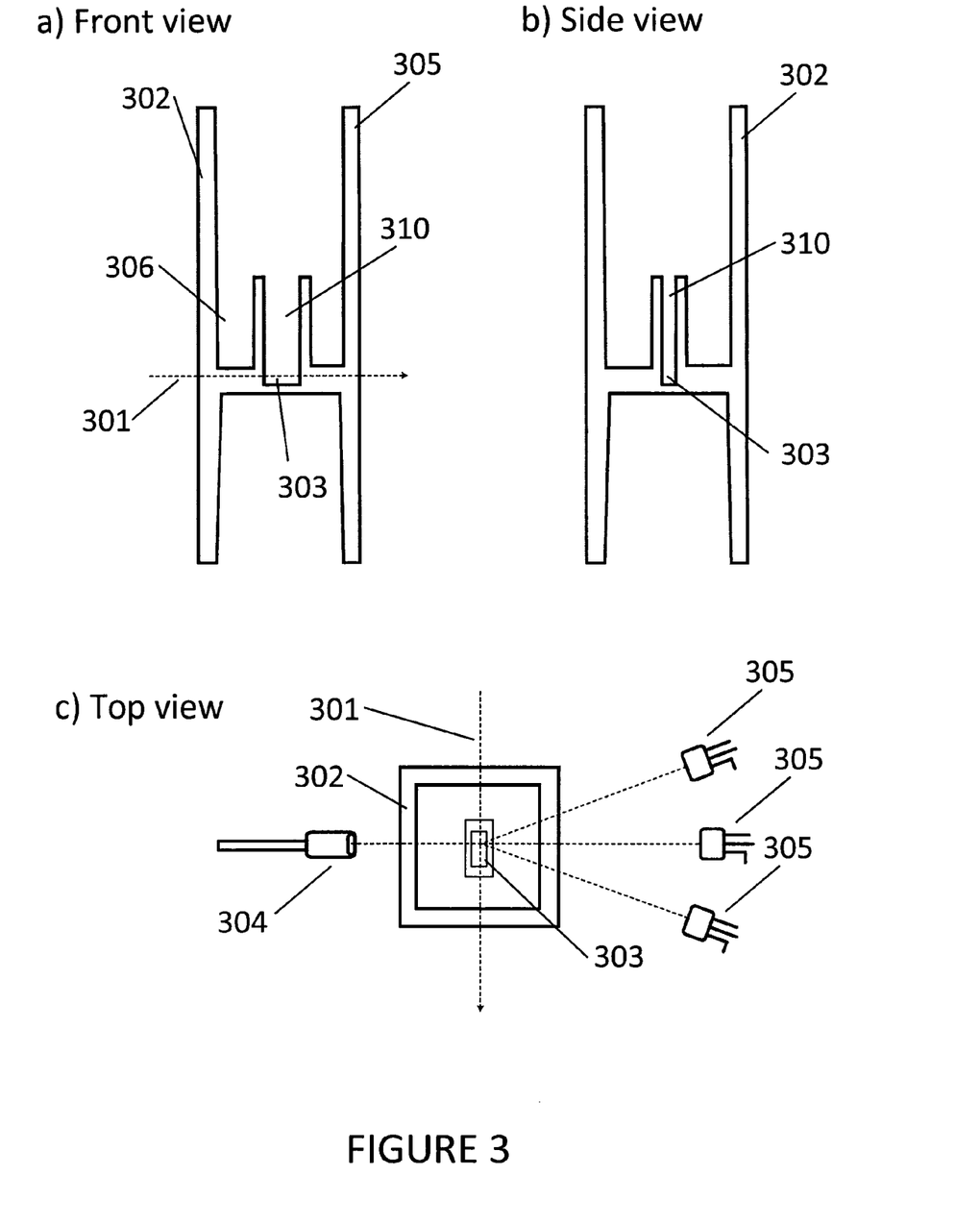
FIG. 3 shows another embodiment of the present invention in cutaway views: front view (a), side view (b), and top view (c), wherein the top view also indicates elements which may be used in light scattering measurements.

In FIG. 3 we show another embodiment of the novel cuvette of the present invention. In contrast to the embodiment shown in FIG. 2, the trough extends as a moat completely encircling the sample chamber which is raised by an intervening wall to allow significant overfill of the sample measurement chamber. If, for example, the sample measurement chamber 303, at the bottom of the sample chamber, has a volume of 44 with dimensions 1 mm height, 4 mm length, and 1 mm depth, with the length being along the path of the beam 301 through the sample, the walls of the sample chamber 310 may extend well above this sample measurement chamber 303, allowing the user to overfill the sample chamber many times over without spilling into the moat. For example, the sample chamber 310 may act as a sample reservoir and allow overfill of the sample measurement chamber by, for example, 700 µL. When this abundance of sample is available, this partially or completely filled expanded sample chamber 310 can aid in mitigating problems associated with evaporation, promote temperature stability of the solution against minor fluctuations of the temperature of the light scattering instrument, and facilitate sample loading. This extended sample chamber/reservoir 310 facilitates capping the sample with immersion oil if that is preferred. When such an abundance of sample is not available, the walls of the sample chamber can still facilitate loading by giving the user a surface against which to rest the end of the dispensing pipette loaded with the minimum necessary amount sample into the sample measurement chamber. In this embodiment, the trough of FIG. 2 becomes a moat 306 surrounding the sample chamber, creating a large surface area of the solvent contained within this moat, thus allowing empty volume within a capped cuvette to reach a saturated vapor pressure quickly. It should be noted that the sample measurement chamber 303 extends below the level of the moat 306, allowing the beam 301 to pass through optically transparent elements of the cuvette 302 without intersecting the moat 306. DLS and SLS detectors, 304 and 305 respectively, can be arranged around the cuvette in the plane defined by the sample measurement chamber 303 and the beam 301. It should be again noted that while SLS and DLS detectors positioned at 90° to the beam are often preferred, it is not necessary that they be so positioned. It is also not necessary that the DLS detector and/or SLS detector(s) be positioned on opposite sides of the cuvette. Further it is also possible to have one or more of the detectors located off axis from the others, for example, the DLS detector might be located beneath the cuvette. It is also possible that only DLS or SLS detectors will be used, and not both.

Figure 4:
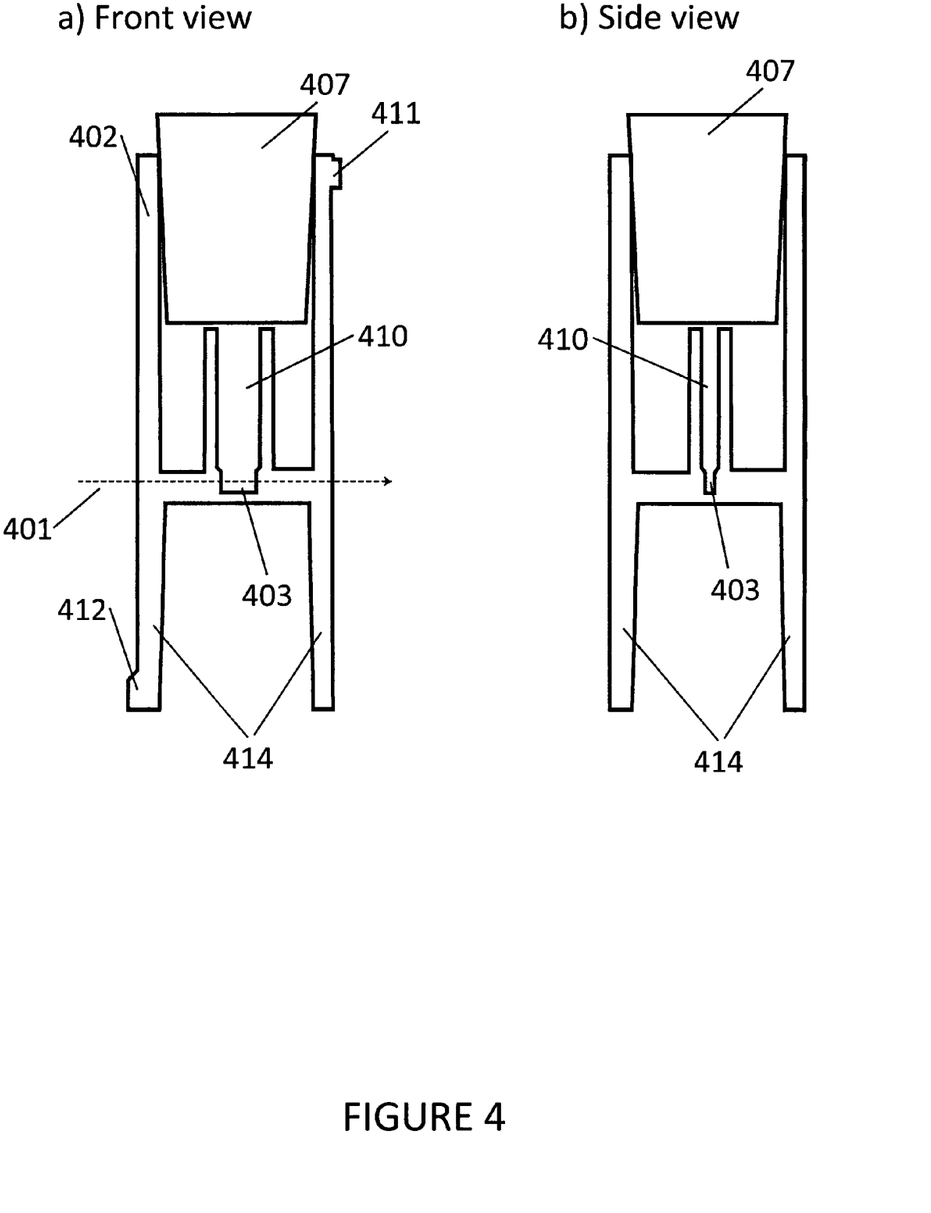
FIG. 4 shows a cutaway of a front view (a) and a side view (b) of another embodiment of the invention.
Figure 5:
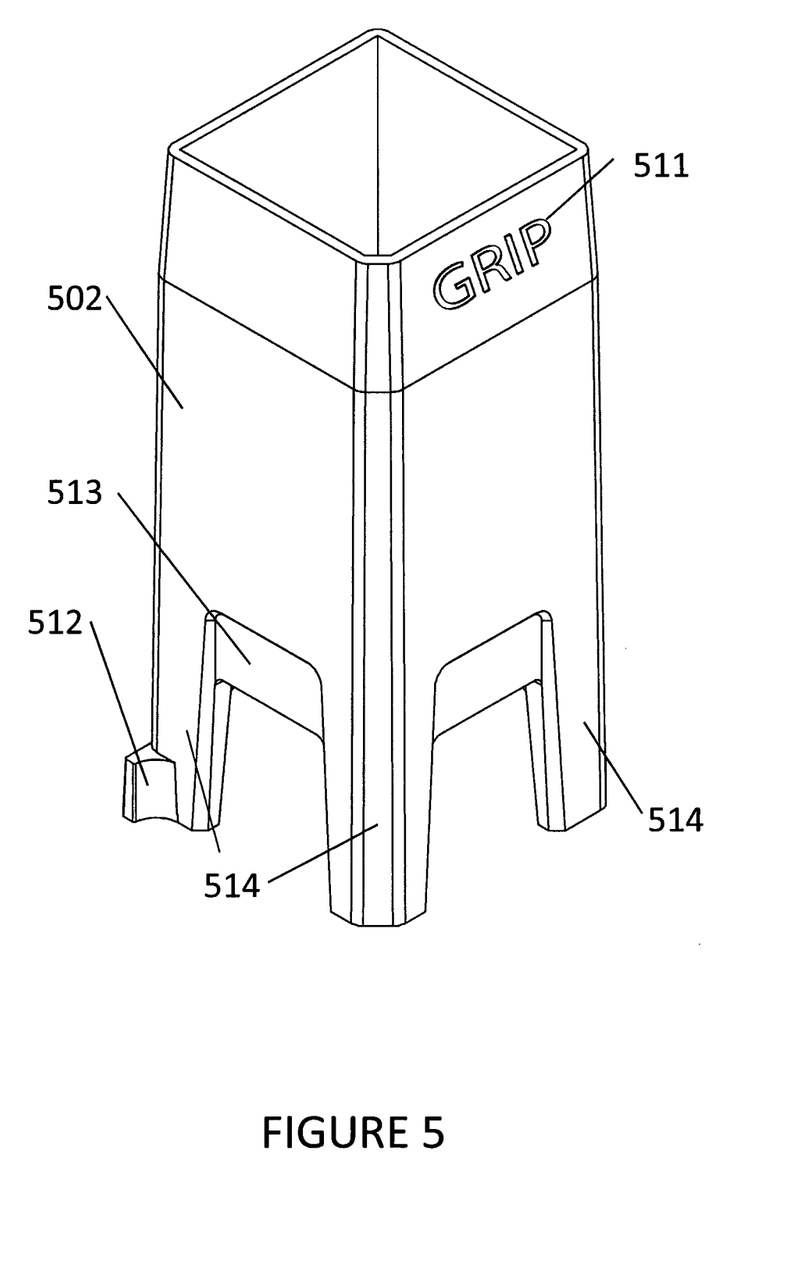
FIG. 5 is a perspective view of an embodiment of the invention similar to that depicted in FIG. 4.

Another embodiment of the inventive cuvette is shown in FIG. 4. In this embodiment, the sample chamber 410 is slightly angled as it nears the sample measurement chamber 403, to facilitate flow from the dispenser into the sample measurement chamber 403. A tall cap 407 is preferably made of a substance, such as silicone, that is unlikely to interact with the solvent. The cap seals against the inner walls of the cuvette body 402 filling much of the volume of the cuvette, creating less empty volume which allows the saturation vapor pressure to be reached much more quickly. A raised area 411 on an outer surface near the rim of the cuvette can facilitate insertion and removal of the cuvette from the light scattering instrument. This raised area 411 may double as a product identification indicator, model number, supplier logo, etc. Other raised or keyed areas 412 may be used to identify a particular model of cuvette used by the light scattering instrument. For example, a cuvette with a 1 mm×1 mm×4 mm sample measurement chamber may be distinguished from a 1 mm×1 mm×2 mm sample measurement chamber by a raised key 412 extending in a particular direction from one of the cuvette legs 414. A perspective view of a similar embodiment, shown in FIG. 5, helps to elucidate more of the possible beneficial elements of the inventive cuvette. The raised grip area 511 may appear on one or more of the faces of the cuvette. Also, the beam passing surfaces 513 may be molded, machined or polished in such a way as to create a small angle with the incident beam such that the beam does not enter the cuvette orthogonally allowing any reflected light to be directed away from the sample or other detectors. The length of the cuvette legs 514 can be chosen to match the light scattering detector for which the cuvette is intended and may also contained keyed elements allowing them to be inserted only in the correct orientation. Further, additional keys 512 may be located on the legs or other parts of the cuvette which may indicate the specifics of the cuvette to a properly programmed light scattering detector. For example, a particular key might indicate to the light scattering instrument, the material from which the cuvette is made, which will trigger the instrument to adjust its allowable temperature control range accordingly so as to disallow the instrument from heating to a temperature which would cause damage to the cuvette.

While one objective of the invention is to permit these cuvettes to be made of a material which can be disposed of after a single use, the invention is not limited to disposable embodiments only. The cuvettes may be made of any material or materials capable of being molded, formed, fused, or otherwise constructed into the proper forms described above.

The cuvettes may also be made of a combination of several materials. In a preferred embodiment, the cuvettes will be molded from Cyclic Olefin Copolymer (COC) which is compatible with aqueous buffers and alcohols, and can be easily and inexpensively injection molded into a cuvette consistent with the present invention. COC is inexpensive and therefore likely permits the cuvettes to act in a disposable capacity, without the need to clean and reuse them.

While many references have been made to light scattering detection throughout this specification, the inventive cuvettes disclosed herein should not be considered limited to use with light scattering detectors. Indeed, variations on the embodiments disclosed above permit the measurement of UV absorption, for example. For such measurements it may be advantageous to offer several different volumes of the sample measurement chamber, with varying lengths associated with path length through which the beam passes corresponding to various concentrations of solution. Similarly, the inventive cuvettes disclosed herein could also be used to measure the turbidity of the solution, and for this purpose also, a varying beam path length over several cuvette models may be advantageous.

There are many embodiments of our invention that will be obvious to those skilled in the arts of measurement optics and evaporation control that are but simple variations of our basic invention herein disclosed that do not depart from the fundamental elements that we have listed for their practice; all such variations are but obvious implementations of the invention described hereinbefore and are included by reference to our claims, which follow.

The invention claimed is:

1. A cuvette with a rectangular cross section for use with a light scattering detector comprising:
   a. a sample reservoir connected to and extending upwards from a sample measurement chamber into which a liquid sample is injected, said sample measurement chamber having the shape of a right rectangular prism;
   b. a moat encircling said sample reservoir into which a second liquid is injected, where said second liquid within said moat is not in liquid contact with said liquid sample contained within said sample reservoir and said sample measurement chamber, wherein, further, a liquid/air interface of said liquid sample in said sample reservoir and measurement chamber is in gaseous contact with a liquid/air interface of said second liquid contained within said moat;
   c. a cap element sealing the opening of said cuvette from the atmosphere outside of the cuvette;
   d. an optically transparent surface through which a beam may pass into said sample measurement chamber; and
   e. at least one additional optically transparent surface through which light scattered from said liquid sample light may pass.

2. The cuvette of claim 1 wherein said cuvette is manufactured from an injection molded polymer.

3. The cuvette of claim 2 wherein said polymer is cyclic olefin copolymer.

4. The cuvette of claim 1 further comprising a plurality of legs so configured as to place said sample measurement chamber within the path of a beam generated within a light scattering detector.

5. The cuvette of claim 1 further comprising an element raised relative to one or more of the outer walls of said cuvette, said raised element providing an improved griping surface.

6. The cuvette of claim 1 further comprising a keyed surface that can indicate to a light scattering detector information regarding the model of said cuvette.

7. The cuvette of claim 1 further comprising one or more elements opaque to the wavelength of said beam.

8. The cuvette of claim 1 wherein said cap extends into said cuvette, occupying at least 50% of the empty volume therein.

9. The cuvette of claim 8 wherein said cap is made of silicone.

10. The cuvette of claim 1 wherein said sample measurement chamber has a volume between 4 µL and 7 µL.

11. The cuvette of claim 1 wherein said sample measurement chamber has a volume less than 4 µL.

12. The cuvette of claim 1 comprising a further optically transparent surface beneath said sample measurement chamber, through which scattered light may pass.

13. The cuvette of claim 1 wherein said cuvette is manufactured of a plurality of materials.

14. The cuvette of claim 13 wherein said sample measurement chamber is manufactured of quartz and where the remainder of the cuvette is manufactured of an injection molded polymer.

* * * * *